(12) United States Patent
Costi

(10) Patent No.: US 12,295,567 B2
(45) Date of Patent: May 13, 2025

(54) SURGICAL TOOL FOR ABDOMINAL SUTURE

(71) Applicant: SMARTCLOSER SURGICAL DEVICES SOCIETA' A RESPONSABILITA' LIMITATA, Parma (IT)

(72) Inventor: Renato Costi, Parma (IT)

(73) Assignee: SMARTCLOSER SURGICAL DEVICES SOCIETA' A RESPONSABILITA' LIMITATA, Parma (IT)

( * ) Notice: Subject to any disclaimer, the term of this patent is extended or adjusted under 35 U.S.C. 154(b) by 0 days.

(21) Appl. No.: 18/000,045

(22) PCT Filed: Jun. 7, 2021

(86) PCT No.: PCT/EP2021/065176
§ 371 (c)(1),
(2) Date: Nov. 28, 2022

(87) PCT Pub. No.: WO2021/249947
PCT Pub. Date: Dec. 16, 2021

(65) Prior Publication Data
US 2025/0017583 A1 Jan. 16, 2025

(30) Foreign Application Priority Data
Jun. 9, 2020 (IT) ......................... 102020000013720

(51) Int. Cl.
*A61B 17/04* (2006.01)
(52) U.S. Cl.
CPC .... *A61B 17/0469* (2013.01); *A61B 2017/047* (2013.01); *A61B 2017/0472* (2013.01)

(58) Field of Classification Search
CPC ............ A61B 17/0469; A61B 17/0472; A61B 2017/047
See application file for complete search history.

(56) References Cited

U.S. PATENT DOCUMENTS

| 5,320,632 | A | | 6/1994 | Heidmueller |
| 5,364,408 | A | * | 11/1994 | Gordon ............ A61B 17/06066 606/139 |

(Continued)

FOREIGN PATENT DOCUMENTS

| EP | 0738127 A1 | 10/1996 |
| WO | 9405213 A1 | 3/1994 |

OTHER PUBLICATIONS

International Search Report and Written Opinion for Corresponding International Application No. PCT/EP2021/065176 (12 Pages) (Sep. 10, 2021).

(Continued)

*Primary Examiner* — Phong Son H Dang
(74) *Attorney, Agent, or Firm* — LUCAS & MERCANTI, LLP

(57) ABSTRACT

A surgical tool for abdominal suturing is disclosed having an elongated body with oval or elliptical cross-section, a distal end, a proximal handle and a lateral pair of notches between the distal end and the proximal handle. The pair of notches is transversally aligned on a major axis of the oval or elliptical cross-section. A pair of needles is housed in the distal end with needle tips directed towards the proximal handle. The pair of needles is configured to longitudinally slide and engage via the needle tips with the pair of notches. The tool also includes a mover device configured to proximally move the pair of needles in engagement with the pair of notches, and to further proximally move the pair of needles beyond the pair of notches.

16 Claims, 6 Drawing Sheets

(56) References Cited

U.S. PATENT DOCUMENTS

| | | | | |
|---|---|---|---|---|
| 5,700,273 A | * | 12/1997 | Buelna | A61B 17/0483 606/144 |
| 5,836,955 A | * | 11/1998 | Buelna | A61B 17/0625 606/144 |
| 6,036,699 A | * | 3/2000 | Andreas | A61B 17/11 606/139 |
| 6,383,208 B1 | | 5/2002 | Sancoff et al. | |
| 6,743,241 B2 | * | 6/2004 | Kerr | A61B 17/0057 606/139 |
| 7,837,696 B2 | * | 11/2010 | Modesitt | A61B 17/0057 606/139 |
| 9,370,353 B2 | * | 6/2016 | Fortson | A61B 17/0469 |
| 2005/0119670 A1 | | 6/2005 | Kerr | |
| 2017/0189061 A1 | | 7/2017 | Weisbrod et al. | |

OTHER PUBLICATIONS

International Preliminary Report on Patentability for Corresponding International Application No. PCT/EP2021/065176 (37 Pages) (Sep. 27, 2022).

* cited by examiner

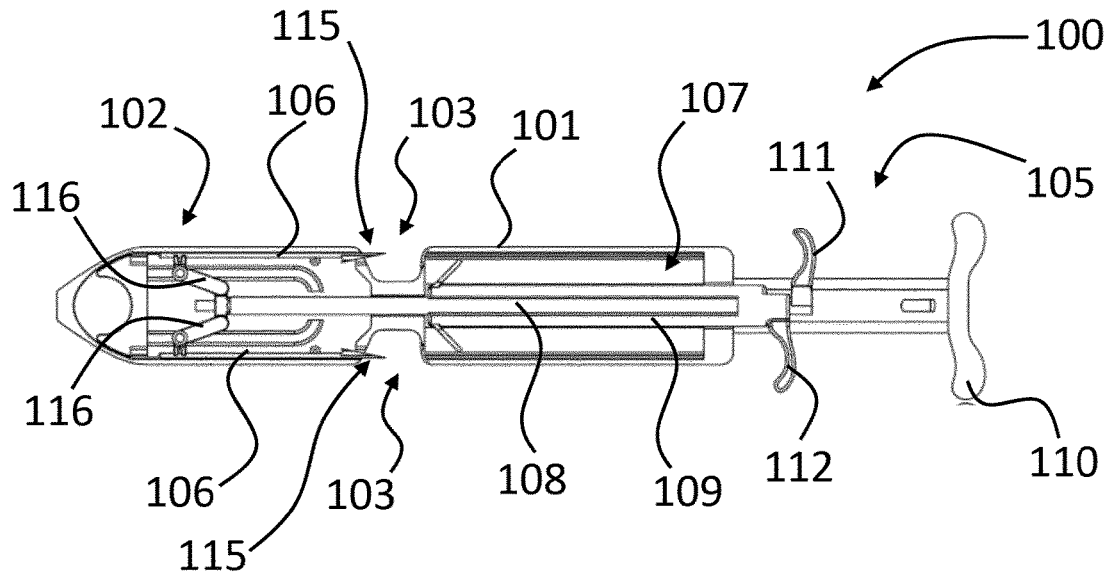
FIG. 6
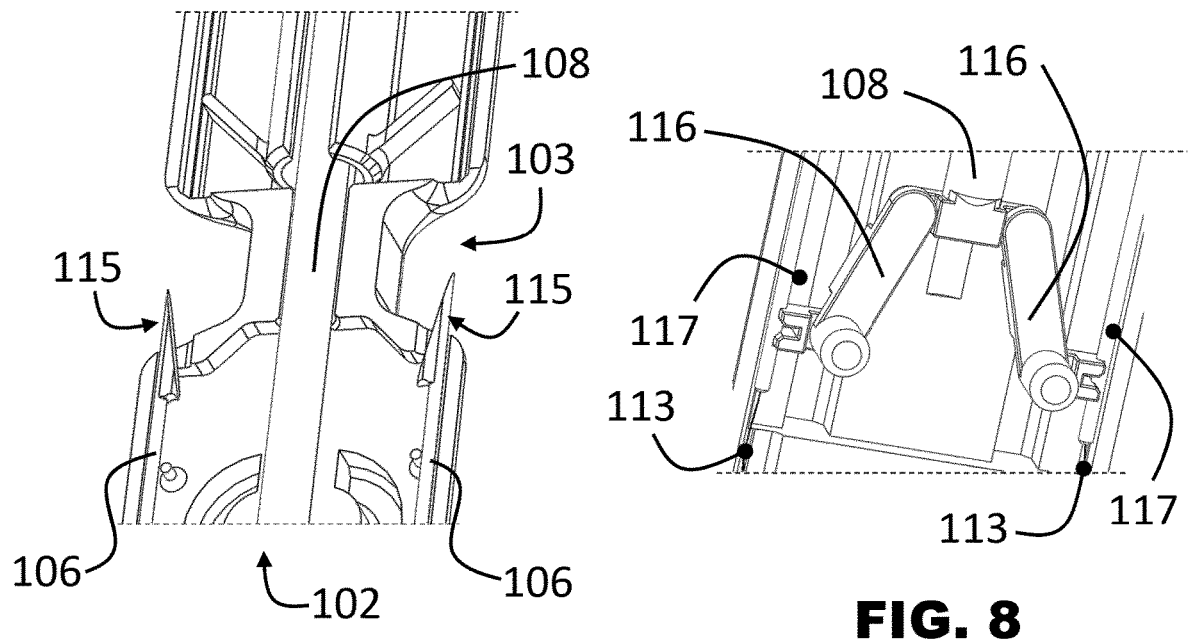
FIG. 7
FIG. 8

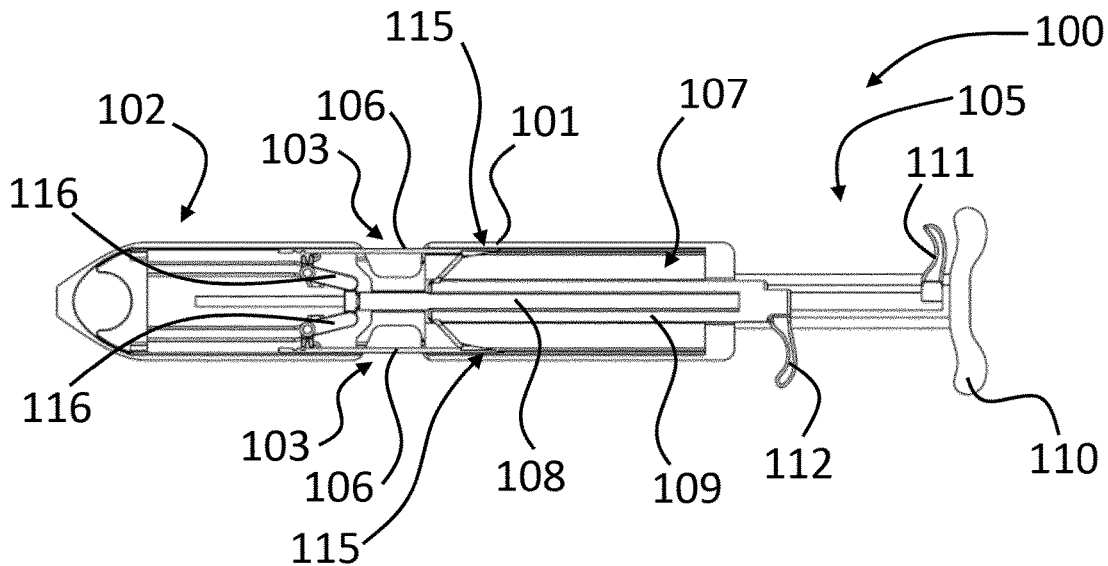
FIG. 9
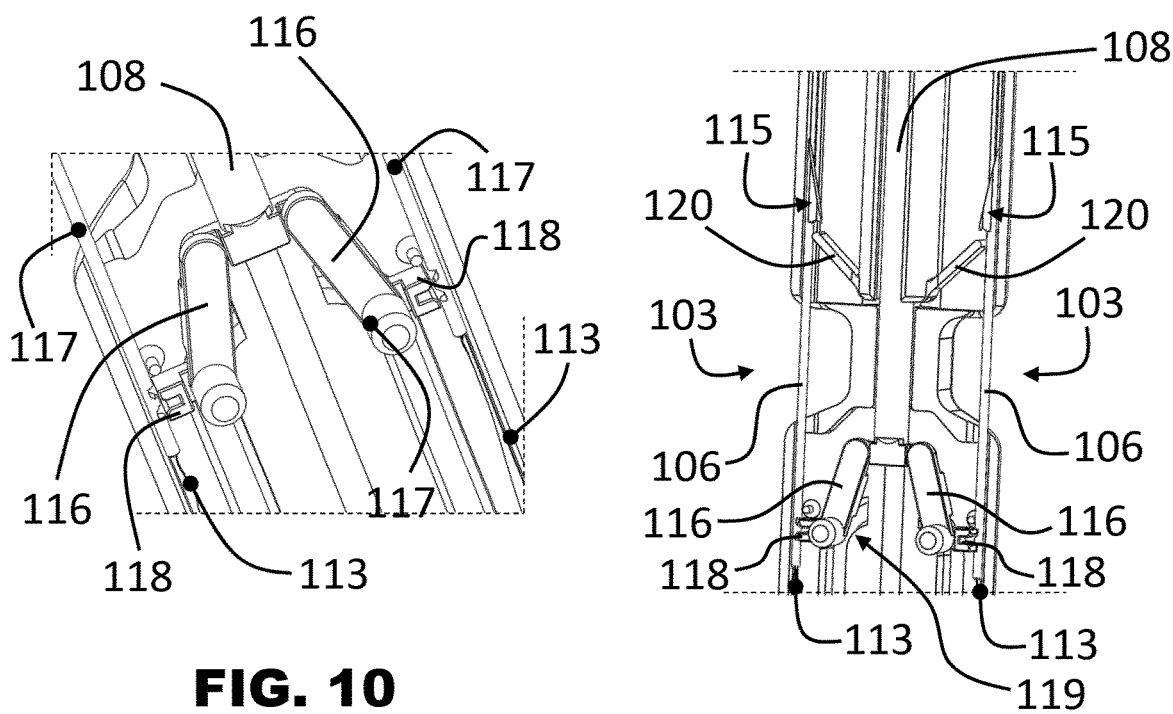
FIG. 10
FIG. 11

SURGICAL TOOL FOR ABDOMINAL SUTURE

CROSS-REFERENCE TO RELATED APPLICATIONS

This application is a 371 of PCT/EP2021/065176, filed Jun. 7, 2021, which claims the benefit of Italian Patent Application No. 102020000013720, filed Jun. 9, 2020.

TECHNICAL FIELD

The present invention relates to a surgical tool for abdominal suture.

In general, the present invention finds application in the field of surgical tools, in particular for closing small incisions in the abdominal wall, especially in connection with laparoscopic procedures.

PRIOR ART

In abdominal surgery, the laparoscopic technique allows surgical operations to be performed avoiding long incisions of the abdominal wall to be made, using on the contrary small incisions (usually 5 to 15 mm long) to introduce, through suitable hollow tools (the "trocars"), a camera and dedicated tools by means of which surgery is performed. The incisions required for trocars' introduction are known as "trocar-sites" or generally also "port-sites".

Surgeries which can be performed to date through the laparoscopic technique are several: cholecystectomy, gastro-oesophageal joint surgery and of morbid obesity surgery, colon surgery, and others.

The trocars, which are hollow-inside cylinder-shaped tools, made of plastic/metal, are positioned at the beginning of surgery through the abdominal wall and they are removed at the end of the procedure, leaving a hole in the patient's abdominal fascia.

If this hole is not properly closed some complications can occur, among which the main one is the "incisional hernia", an abdominal hernia on a cicatrix of a past incision, with the possible protrusion of visceral tissue from the fascia and the occurrence of further complications, such as intestinal obstruction and even intestinal necrosis.

In order to avoid future incisional hernias and related complications, it is necessary to close, manually or by means of traditional or dedicated laparoscopic tools, the hole left by the trocar, particularly by suturing the abdominal wall layer called muscular-aponeurotic fascia (or most commonly "fascia").

Closing the trocar-sites at the end of the surgical procedure often poses a technical problem linked to the fact that the skin incision has the same length as the fascial one, thus limited in this case, making it difficult even just to "see" the orifice in the fascia through the skin orifice, and thus making it extremely difficult to reach the fascia and to properly suture it. This problem is even more serious for obese patients, where the thicker adipose layer spaces the skin orifice further apart from the fascial one.

As stated, this difficulty in closing the trocar-sites occurs at the end of surgery, which can last up to several hours, when the surgical team is tired. This often results in an operation which is sometimes poorly performed or not performed at all or in proxying such manoeuvre seen as "routine" to the surgeon's assistants, who are generally less skilled.

Known techniques for closing the abdominal wall include "internal" closing techniques, which require two additional port-sites; "external" techniques, which require an additional port-site; techniques with or without display, with no additional port-sites. Besides "manual" closing techniques, several devices for closing the abdominal wall were proposed: spinal puncture needle, hypodermic injection needle, Deschamps needle, Berci needle, aneurysm needle.

None of these techniques, which are too complex and/or time-consuming, proved satisfactory and became universally recognized as a "gold-standard" for closing port-sites after laparoscopic surgery.

SUMMARY OF THE INVENTION

Object of the present invention is to remedy the drawbacks of known techniques.

A particular object of the present invention is to allow the peritoneum and the fascia to be closed in few seconds.

A further particular object of the present invention is to give the greatest safety guarantee in a laparoscopic surgery situation.

A further particular object of the present invention is to allow a suture thread to be positioned in the most correct position in the fascial incision.

A further particular object of the present invention is to provide an ergonomic device which can be used with few and simple gestures.

These and other objects are achieved by a surgical tool for abdominal suture according to the features of the appended claims forming an integral part of the present disclosure.

An idea underlying the present invention is to provide a surgical tool which is composed of several parts, whose movement is aimed at causing passage of suture needles, initially contained in a distal portion of the tool itself, through the abdominal wall, and the recovery thereof in a tool proximal 'tail'.

In an embodiment, the present invention provides a surgical tool for abdominal suture, comprising: an elongated body comprising a distal end, a proximal handle and a lateral pair of notches in between the distal end and the proximal handle, the elongated body having an oval or elliptical cross-section, wherein the pair of notches are further transversally aligned on a major axis of the oval or elliptical cross-section; a pair of needles housed in the distal end with needle tips directed towards the proximal handle and configured to longitudinally slide and engage with the needle tips the pair of notches; a suture thread with respective terminations fixed to the pair of needles; a mover device configured to proximally move the pair of needles in engagement with the pair of notches, and further configured to further proximally move the pair of needles beyond the pair of notches.

Advantageously, the surgical tool according to the present invention allows the surgeon to perform in few seconds an easy closing of the incision which the trocar leaves in the abdominal fascia, facilitating the operator in practicing this gesture, directly contributing to increasing the number of sutures performed and the quality thereof, and thus representing an advantage for the patient, for the surgeon and for the healthcare system itself.

Advantageously, the surgical tool according to the present invention allows, with a minimal and ergonomic movement, the needle to rapidly pass through the abdominal wall fascia in the correct position and, once extracted, it leaves to the surgeon the two thread ends to be knotted for an efficient closing of the abdominal wall.

Preferably, the proximal handle, connected to the elongated body, is operable by the surgeon. The mover device, comprises two rods: a first rod configured for removable connection to the pair of needles, to proximally move it in engagement with the pair of notches; a second rod configured for further connection to the pair of needles, to further move it, in a more proximal position with respect to the pair of notches.

Preferably, the first rod and the second rod are at least partially internal to the body of the surgical tool and are coaxial, and the surgical tool comprises a pair of triggers which are associated with the proximal handle and conveniently operable by the surgeon.

Further features and advantages will be more apparent from the following detailed description of preferred non-limiting embodiments of the present invention, and from the dependent claims which outline preferred and particularly advantageous embodiments of the invention.

BRIEF DESCRIPTION OF THE DRAWINGS

The invention is illustrated with reference to the following figures, given by way of non-limiting examples, in which:

FIG. 6 illustrates a cross-sectional view of the surgical tool in a second operating mode.

FIG. 7 illustrates a detail of the surgical tool in the second operating mode.

FIG. 8 illustrates a further detail of the surgical tool in the second operating mode.

FIG. 9 illustrates a cross-sectional view of the surgical tool in a third operating mode.

FIG. 10 illustrates a detail of the surgical tool in the third operating mode.

FIG. 11 illustrates a further detail of the surgical tool in the third operating mode.

In the different figures, similar elements will be identified by similar reference numbers.

DETAILED DESCRIPTION

Figure 1:
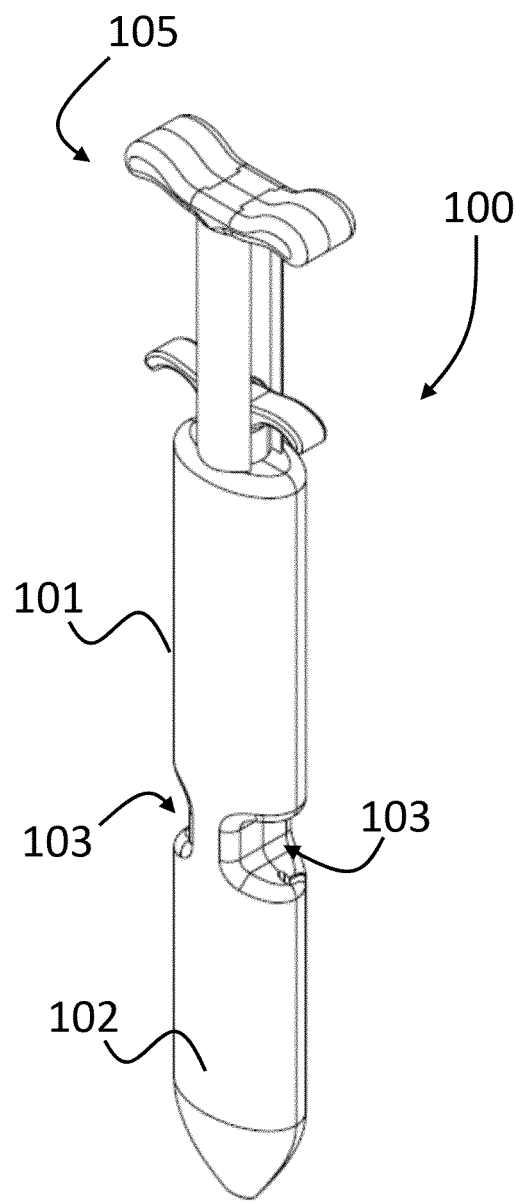
FIG. 1 illustrates a perspective view of an embodiment of surgical tool according to the present invention.

FIG. 1 illustrates a perspective view of an exemplary and non-limiting embodiment of the surgical tool 100 for abdominal suture according to the present invention.

The surgical tool 100 comprises an elongated body 101, having a distal end 102 and a lateral pair of notches 103.

A pair of needles (not visible) is housed in the distal end 102 and is configured to longitudinally slide and engage the pair of notches 103 by respective needle tips, with modes which will be described hereafter.

The distal end 102 has an ogival profile and is configured for insertion in a hole passing through an abdominal wall.

In order to conform to the anatomy of the abdominal fascia, the lateral notches 103 are on opposite sides of the elongated body 101 and are longitudinally aligned to each other.

Moreover, the lateral notches 103 are tapered with respect to the elongated body 101 to facilitate the insertion and extraction of the surgical tool 100 in a hole passing through an abdominal wall.

Figure 2:
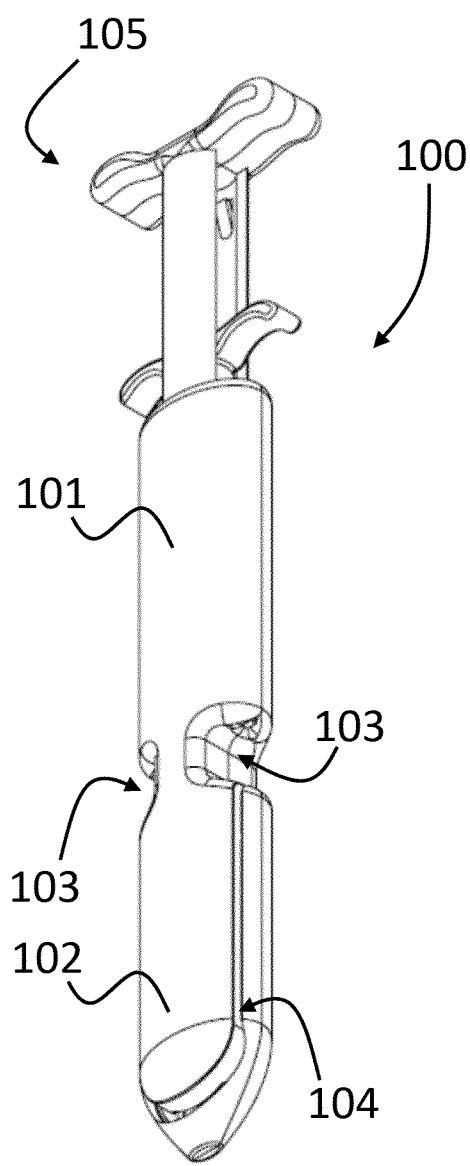
FIG. 2 illustrates a further perspective view of the surgical tool.

FIG. 2 illustrates a further perspective view of the surgical tool 100.

This view highlights how, laterally on the distal end 102, there is a slot 104 joining the pair of notches 103, with the aim of slipping a suture thread according to modes which will be further described.

The external shell of the surgical tool 100, which includes the distal end 102, is an envelope made of a stiff and smooth material (probably a high-density polymer), having an elongated shape, a rounded tip and an oval or elliptical cross-section, connected to a T-shaped handle 105 in the proximal end thereof.

As it can be seen, the pair of notches 103 is in between the distal end 102 and the proximal handle 105.

As it can be further seen, the pair of notches 103 are further transversally aligned on a major axis of the oval or elliptical cross-section of the surgical tool 100.

In the present description, reference will be made to a device configuration of use in which the parts referred to as "proximal" are those being closest to the surgeon which grasps the surgical tool, while the parts referred to as "distal" are those being farthest from the surgeon and intended to contact the patient.

The surgical tool 100 has thereinside several hollow spaces which allow the movement of rods, needles and articulated arms, besides the suture thread, according to modes which will be described hereafter.

It should be noted that the suture thread, although it is conceptually present, will be represented only in some of the figures, for a graphical simplification.

The external surface of the elongated body 101 has, as stated, two peculiarities: the deep incisions 103 on the lateral wall of the tool 100 at about half of the longitudinal axis, intended to receive the margin of the orifice that the trocar has left in the fascia, which will have in turn to be pierced by the needles; the thin slot 104 which actually joins in the distal part 102 of the tool 100 the two incisions 103, which allows the suture thread to be freed from the tool 100 upon extraction thereof. In the most distal portion 102, there is, inside the tool 100, a tank for the suture thread.

Figure 3:
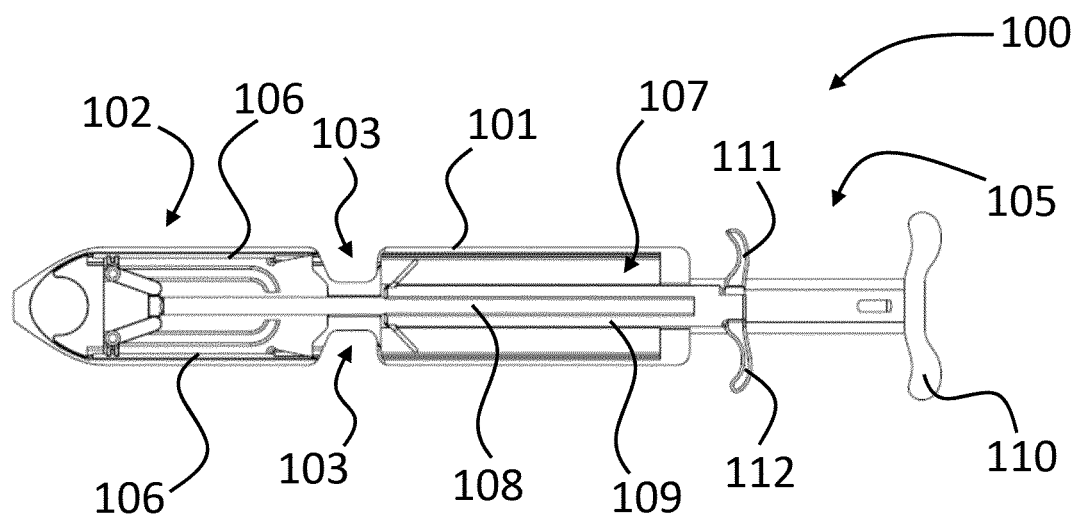
FIG. 3 illustrates a cross-sectional view of the surgical tool in a first operating mode.

FIG. 3 illustrates a cross-sectional view of the surgical tool 100 in a first operating mode called "open".

In this view a pair of needles 106 housed in the distal end 102 can be seen, which, as it will be further described, are configured to longitudinally slide with respect to the elongated body 101, in an approaching direction with respect to the proximal handle 105 connected to the elongated body 101, and thereby to engage, with the respective needle tips, the pair of notches 103.

As it can be seen, the pair of needles 106 housed in the distal end 102 have needle tips directed towards the proximal handle 105.

The surgical tool 100 further comprises a mover device 107 (or "pusher and puller device" 107), configured to proximally move (or "push") the pair of needles 106 in engagement with the pair of notches 103, and further configured to further move (or "retract") the pair of needles 106 proximally, beyond the pair of notches 103, after passing through the fascia engaged in the notch 103, thereby allowing the abdominal wall to be sutured.

The mover device 107 comprises a first rod 108 ("pusher rod" 108) which is operable by the handle 105. The first rod 108 is configured to allow a removable connection with the pair of needles 106, at the distal end of the device, to proximally move (or "push") the pair of needles 106 in engagement with the pair of notches 103, as it will be further described.

The mover device 107 further comprises a second rod 109 ("puller rod" 109), which is always operable by the handle 105. The second rod 109 is configured to allow a further connection to the pair of needles 106, to further move (or "retract") it when the pair of needles 106 will have reached a more proximal position with respect to the pair of notches, as it will be further described.

It should be understood that the exemplificative terms "push" and "retract" are related to a direction which is axial and oriented like the needle tip, from the inside of the fascia to the outside, but beyond any doubt they are terms which are evident for the skilled person who takes into consideration a 'sartorial' analogy where the needle is "pushed" by a thimble (analogous to the first rod of the invention) through a fabric and "retracted" by a fingers' grasp (analogous to the second rod of the invention) by the tailor.

Figure 4:
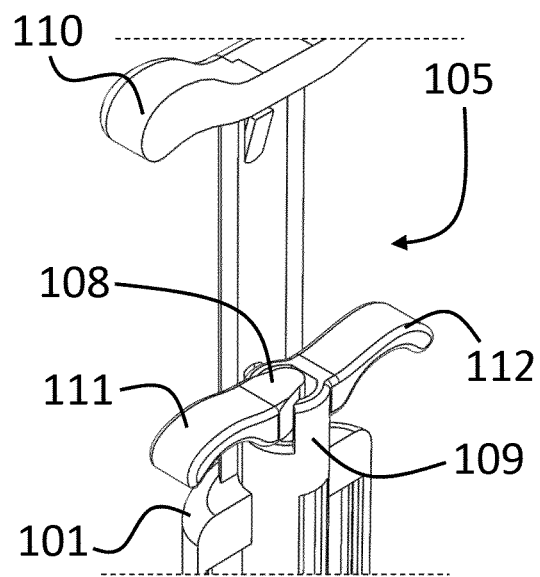
FIG. 4 illustrates a detail of the surgical tool in the first operating mode.

FIG. 4 illustrates a detail of the surgical tool 100 in the first operating mode called "open".

In a preferred embodiment, the first rod 108 and the second rod 109 are at least partially internal to the elongated body 101 and are coaxial to each other. In particular, the first rod 108 is longer, going up to the distal end 102, and it is internal to the second rod 109, which is instead shorter and external.

The proximal handle 105 comprises a fixed element 110, which is preferably T-shaped, and a pair of triggers 111 and 112 which are operable by traction with respect to the fixed element 110, as it will be further described.

The triggers are associated with the first rod 108 for the trigger 111, and with the second rod 109 for the trigger 112, respectively.

Figure 5:
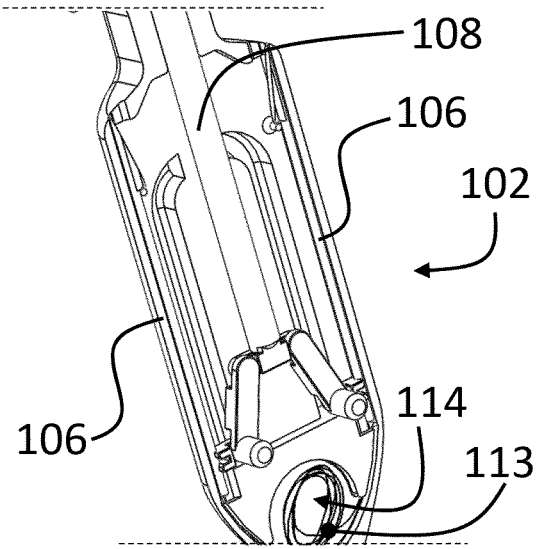
FIG. 5 illustrates a further detail of the surgical tool in the first operating mode.

FIG. 5 illustrates a further detail of the surgical tool 100 in the first operating mode called "open".

A suture thread 113 with respective terminations fixed to the pair of needles 106, preferably housed in a tank 114 of the distal end 102, is represented in this image.

In this first operating mode called "open", the operation of the surgical tool 100 can be described as follows.

The distal end 102 of the surgical tool 100 is inserted through a skin hole left by a trocar.

In particular, during initial insertion the major axis of the oval or elliptical cross-section of the surgical tool 100 is kept parallel to the trocar incision's longitudinal major axis in the fascia.

The distal end 102 of the surgical tool 100 is then pushed through the abdominal wall layers, reaching the abdominal cavity, particularly under video-laparoscopic control.

Under video-laparoscopic visual control, the surgeon rotates and orients the major axis of the cross section of the surgical tool 100 (being it oval or elliptical) in a position which is perpendicular to the trocar incision's longitudinal major axis in the fascia, i.e., to the progression of the incision of the trocar in the fascia.

Thus, the oval or elliptical cross-section of the surgical tool 100 allows the lateral notches 103 to better include the fascia's margins of the trocar incision, which will be positioned exactly in the central incision 103 of the surgical tool 100, for subsequent suture.

In this operating mode, the needles 106 are fully contained in the distal end 102 of the tool.

FIG. 6 illustrates a cross-sectional view of the surgical tool 100 in a second operating mode called "bite".

As described, the first rod 108 is operable by the handle 105 and is configured to have a removable connection to the pair of needles 106, to proximally move (or "push") it in engagement with the pair of notches 103.

In a preferred embodiment, the first rod 108 is a cylinder made of a stiff material, probably metal, which is in the innermost position of the surgical tool 100. This first rod 108 is connected at the distal end thereof to two articulated arms 116 which have the function of transmitting the movements from the first rod 108 to the needles 106, as it will be further described. The proximal end of the first rod 108 is characterized by an L-shaped handle which forms the trigger 111, which is operable by the traction of the surgeon's forefinger.

FIG. 7 illustrates a detail of the surgical tool 100 in the second operating mode called "bite", in which it can be seen that the needles 106 comprise respective needle tips 115 which are configured to engage first the pair of notches 103.

As it can further be seen, the needle tips 115 are pointed to and directed towards the proximal handle 105. FIG. 8 illustrates a further detail of the surgical tool 100 in the second operating mode called "bite", in which it can be seen that the pair of needles 106 comprises respective needle stems 117, which are parallel to and opposite each other, and that the arms 116 of the first rod 108 are configured for removable connection to the needle stems 117, as it will be further described.

In particular, the arms 116 connect the first rod 108 to the needles 106; in the proximal part thereof they are in fact connected to the distal end of the first rod 108, while at the distal end thereof they are interlock-shaped, preferably a double square-shaped interlock, which connects them to the needle stems 117.

In this second operating mode called "bite", the operation of the surgical tool 100 can be described as follows.

By pulling the trigger 111, the surgeon starts letting the needles 106 proximally slide towards him; these needles 106 slightly protrude in the notches 103 until they find a first reversible block point.

In this "bite" position, the needle tips 115 of the needles 106 are visible by means of a video camera inside the abdomen, thus "from below" or from the distal end of the tool 100, allowing the surgeon to direct them towards the point of the abdominal fascia he deems more suitable, synchronously for both the needles 106. The suture thread, connected to the distal ends of the needle stems 117, starts unwinding.

FIG. 9 illustrates a cross-sectional view of the surgical tool 100 in a third operating mode called "closed".

As described, the second rod 109 is operable by the handle 105 and is configured for further connection to the pair of needles 106, once the corresponding needle tip 115 has passed through the respective notch 103, to further move the pair of needles 106 to a more proximal position with respect to the pair of notches.

In fact, the first rod 108, beside comprising first blocks adapted to reversibly engage the pair of notches 103 with the needle tips 115, further comprises second blocks further adapted to irreversibly disengage from the needle stems.

FIG. 10 illustrates a detail of the surgical tool 100 in the third operating mode called "closed".

As described, the arms 116 are configured to engage with the needle stems 117 so as to transmit a movement from the first rod 108 to the pair of needles 106.

Moreover, the arms 116 are configured to disengage from the needle stems 117, decoupling them from the first rod 108. For this purpose, in a preferred embodiment, the arms 116 comprise articulated arms 116 having arm ends 118 configured to engage with respective surfaces of the needle stems 117.

FIG. 11 illustrates a further detail of the surgical tool 100 in the third operating mode called "closed".

The elongated body 101 further comprises a hollow element 119 which is configured to deflect the arm ends 118, particularly acting on the articulated arms 116. In a preferred embodiment, the interposing element 119 is a hollow element which serves as a track or guide, and which has a medially curved progression in the proximal end thereof, in order to deflect the arm ends 118.

In this way, the arm ends 118, which were engaged with the respective surfaces of the needle stems 117, can be disengaged from the needle stems 117, thereby decoupling the first rod 108 from the needles 106.

The second rod 109 thus comprises block elements 120, which are configured to snap connect, or furthermore to connect by other safety mechanical connection, with the needle tips 115.

For this purpose, the pair of needles 106 comprises respective projecting portions or nicks close to the needle tips 115. In a preferred embodiment, the needles 106 have an asymmetric tip, which is vertical in the lateral part and slanting in the medial part; below the needle tip 115, in a medial position, they have a curve-shaped incision, intended to receive the end of the block elements 120, after the needles 106 have passed through the notches 103, have then pierced the abdominal fascia and have then entered the proximal part of the elongated body 101. In the distal portion, the needles 106 have a double square-shaped medial incision, intended to receive the distal end 118 of the articulated arms 116. The distal end of the needle 106 continues with the suture thread 113.

In particular, the block elements 120 comprise a pair of flexible elements or tabs, configured to engage and block the projecting portions or nicks of the needles 106.

Preferably, the needles 106 are positioned in the laterally outermost part of the surgical tool 100, at the external lateral margins of the distal end 102, in order to facilitate the suture of the abdominal fascia and the following removal of the surgical tool 100 from the "trocar-site".

In this third operating mode called "closed", the operation of the surgical tool 100 can be described as follows.

When the surgeon is satisfied with the positioning of the needles 106 with respect to the abdominal fascia, he begins to pull the trigger 111 of the first rod 108, forcing the reversible block thereof, so as to pierce the abdominal fascia with the needle tips 115; the needles 106 continue the sliding travel, retuning in the elongated body 101 in the proximal part thereof.

Finally, by pulling the trigger 111 of the first rod 108 up to the end stroke, an irreversible block is preferably engaged, and the needles 106 engage in suitable block elements 120 of the second rod 109.

The needles 106, whose needle tip 115 is returned in the proximal part of the elongated body 101, have a respective curved incision at the base of the needle tip 115 which is at the lateral margin of the tab 120 of the second rod 109. At this point, the tab 120 blocks the respective needle tip 115 and prevents the return thereof.

Simultaneously, the articulated arms 116 connected to the distal end of the first rod 108 have decoupled from the needles 106, following the curved profile of the interposing element 119 obtained in the distal part of the elongated body 101 of the surgical tool 100. The needles 106 are now anchored to the surgical tool 100 exclusively through the tabs 120 of the second rod 109, while the suture thread 113 continues to unwind.

Figure 12:
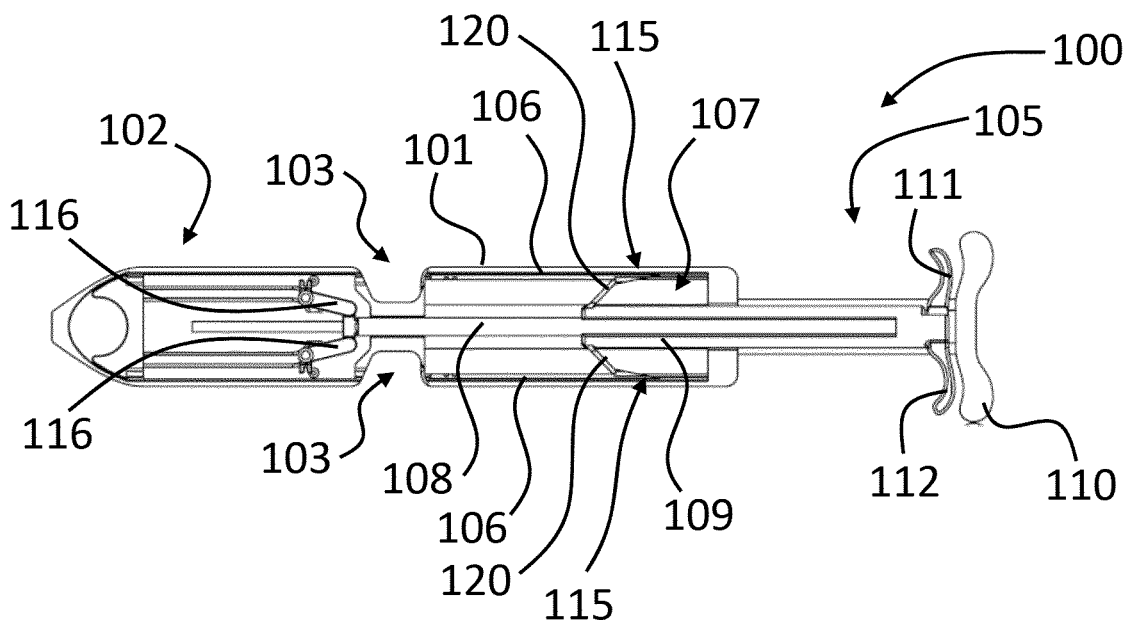
FIG. 12 illustrates a cross-sectional view of the surgical tool in a fourth operating mode.

FIG. 12 illustrates a cross-sectional view of the surgical tool 100 in a fourth operating mode called "swallow".

As already mentioned, the second rod 109 comprises third blocks, adapted to irreversibly keep the pair of needles 106 in a completely retracted position in the proximal part of the elongated body 101.

In a preferred embodiment, the second rod 109 consists of a hollow cylinder made of a stiff material such as for example a high-density polymer, which coaxially houses thereinside the first rod 108. Unlike the first rod 108, the second rod 109 is entirely in the proximal portion of the elongated body 101 and the function thereof is precisely to recover the needles 106 once they have pierced and passed through the abdominal fascia, fitting the suture thread 113 therein in the position decided by the surgeon. In particular, the second rod 109 comprises at the distal end thereof two tabs 120, configured to block the needles 106 and to allow them to be recovered once they pierced the abdominal fascia. The proximal end of the second rod 109 has an L-shaped handle which forms the trigger 112.

Figure 13:
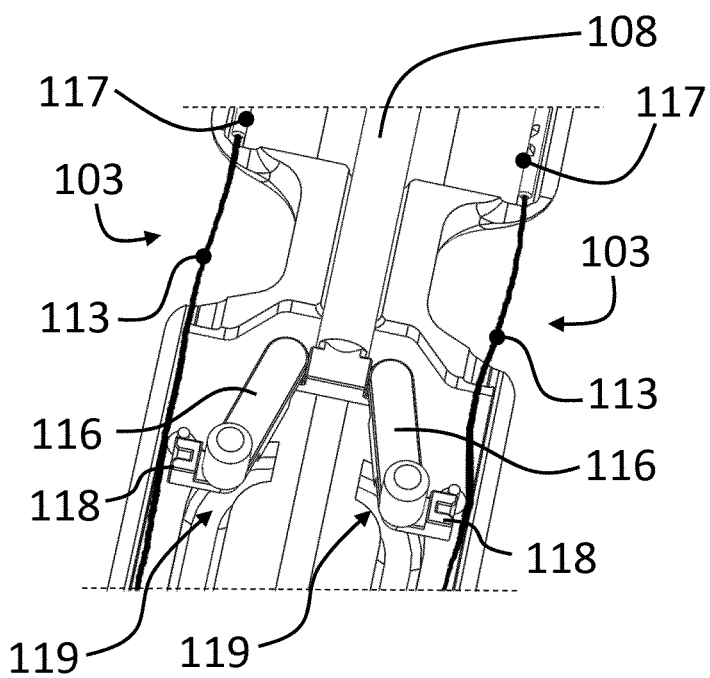
FIG. 13 illustrates a detail of the surgical tool in the fourth operating mode.

FIG. 13 illustrates a detail of the surgical tool 100 in the fourth operating mode called "swallow".

The two ends of the suture thread 113 are in line with the distal end of the needle stems 117. Before starting the movement of the needles 106, the suture thread 113 is contained in a dedicated tank 114, in the distal end 102 of the surgical tool 100; when the needles 106 start the movement thereof under the action of the rods 108 and 109, the suture thread 113 progressively unwinds.

The suture thread 113 continues to unwind until the needles 106, after passing through the abdominal fascia, after returning in the proximal part of the elongated body 101, and after being completely retracted next to being blocked by the tabs 120 of the second rod 109, have terminated their movement. At this point the surgical tool 100 is extracted from the "trocar-site" and the suture thread 113, which has passed through the abdominal fascia (not represented in the figure) following the needles 106, is freed through the slot 104, as it will be further described.

In this fourth operating mode called "swallow", the operation of the surgical tool 100 can be described as follows.

By pulling the trigger 112 connected to the second rod 109, the surgeon progressively recovers the needles 106 which, after passing through the abdominal fascia which will be from now on pierced only by the suture thread 113, now slide in the proximal part of the elongated body 101. The needles 106 completely return in the elongated hollow body of the surgical tool 100. An additional irreversible block at the end stroke of the second rod 109 ends this phase, in which the thread, now engaged in the fascia on both sides, completely unwinds by this time.

Figure 14:
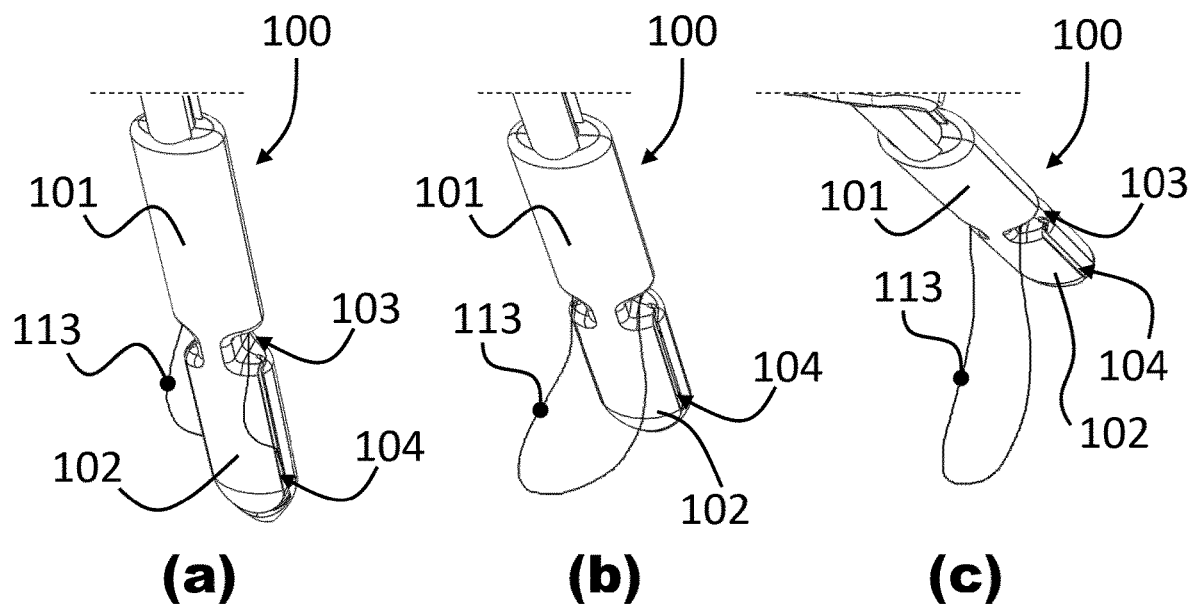
FIG. 14 illustrates three operating conditions of the surgical tool in a fifth operating mode.

FIG. 14 illustrates three operating conditions of the surgical tool 100 in a fifth operating mode called "free".

As described, the suture thread 113 is laterally slippable from the distal end 102 of the elongated body 101. In particular, the distal end 102 comprises a slot 104 joining the pair of notches 103 and configured to laterally slip and free the suture thread 113, originally housed in the tank 114 of the distal end 102.

Figure 15:
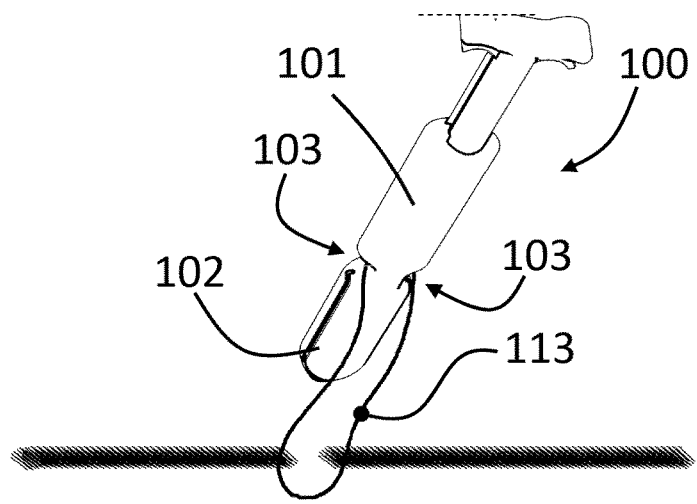
FIG. 15 illustrates a further operating condition of the surgical tool in the fifth operating mode.

FIG. 15 illustrates a further operating condition of the surgical tool 100 in the fifth operating mode called "free".

In particular, from this image it can be appreciated that the lateral notches 103 of the surgical tool 100 are precisely configured to receive the fascia margins of the abdominal wall, so that it is possible to pass through them with the pair of needles 106, which pierce the fascia leaving the suture thread 113 in the position desired by the surgeon to be then retracted in the elongated body 101, and allowing the thread 113 to be freed through the slot 104 to allow the surgical tool 100 to be removed from the "trocar-site".

In this fifth operating mode called "free", the operation of the surgical tool 100 can be described as follows.

With the needles 106 blocked in the proximal position inside the elongated body 101 after passing through the fascia and releasing the suture thread 113, the surgical tool 100 is removed from the abdominal wall. The suture thread 113 in the distal end thereof, has protruded from the distal end 102 of the surgical tool 100 through the slot 104, and is by now exclusively anchored to the abdominal fascia. The suture is completed by simply cutting the suture thread 113 close to the surgical tool and by knotting the two ends of the suture thread 113 anchored only to the fascia at this time.

It is thus evident that the surgical tool according to the present invention allows the surgeon to perform in few seconds an easy closing of the "trocar-site": at first by a rapid and accurate passage of the needles through the abdominal wall fascia, in the correct position, and once the tool has been extracted, by leaving to the surgeon the two ends of the thread to be knotted for an efficient closing of the abdominal wall.

Taking into consideration the here-reported description, the person skilled in the art will be allowed to formulate further modifications and alternatives, in order to meet contingent and specific requirements.

For example, the T-shaped handle with two triggers could be replaced by one having an even more ergonomic shape, such as a "pistol grip".

For example, the needles could be translated by a rod having any shape and size and at any point belonging to the needle length.

For example, the needles could have projections as well as recesses, for connection to the respective mover rods; in particular, the needles need not to have an asymmetrical tip.

For example, the central narrowing, where the fascia to be sutured is inserted defined by the lateral notches, could have more or less rounded shoulders, to facilitate the exiting of the tool, consistently with the length of the needles.

For example, the slot which allows spillage of the suture thread could follow paths which are more or less close to the apex of the tool.

For example, the suture thread can be connected to the lower extreme of the needle as well as go alongside it for a certain part of its length and connect therewith closer to the tip.

For example, the movement of each of the needles could be individually controlled by a mover device comprising one or more rods dedicated to each needle.

Finally, for example, the surgical tool could be equipped with two or more pairs of needles and respective notches, individually or simultaneously controlled by a mover device.

The here-described embodiments are hence to be considered as illustrative and non-limiting examples of the invention.

The invention claimed is:

1. A surgical tool for abdominal suture, comprising:
an elongated body comprising a distal end and a proximal handle, and further comprising a lateral pair of notches in between said distal end and said proximal handle, said elongated body having an oval or elliptical cross-section, wherein the pair of notches are further transversally aligned on a major axis of said oval or elliptical cross-section;
a pair of needles housed in said distal end having needle tips directed towards said proximal handle, said pair of needles being configured to longitudinally slide and engage said needle tips with said pair of notches;
a suture thread with respective terminations fixed to said pair of needles; and
a mover device configured to proximally move said pair of needles in engagement with said pair of notches, and further configured to further proximally move said pair of needles beyond said pair of notches, wherein said mover device comprises:
a first rod, which is operable by said proximal handle and configured for removable connection to said pair of needles, to proximally move said pair of needles in engagement with said pair of notches; and
a second rod, which is operable by said proximal handle and configured for further connection to said pair of needles, to further move said pair of needles in a more proximal position with respect to said pair of notches.

2. The surgical tool according to claim 1, wherein said pair of needles comprises respective needle stems, which are parallel to and opposite each other, and wherein said first rod comprises arms configured for removable connection to said needle stems.

3. The surgical tool according to claim 2, wherein said arms are configured to engage with said needle stems and transmit a movement from said first rod to said pair of needles, and further to disengage from said needle stems decoupling them from said first rod.

4. The surgical tool according to claim 3, wherein said arms comprise articulated arms having arm ends configured to engage with respective surfaces of said needle stems, and wherein said elongated body further comprises an interposing element configured to deflect said arm ends for disengaging said arm ends from said needle stems.

5. The surgical tool according to claim 3, wherein said first rod is configured to reversibly engage said pair of notches with said needle tips and is further configured to irreversibly disengage from said needle stems.

6. The surgical tool according to claim 1, wherein said second rod comprises block elements configured for snap or safety connection with said needle tips.

7. The surgical tool according to claim 6, wherein said second rod is further configured to irreversibly keep said pair of needles in a completely retracted position.

8. The surgical tool according to claim 6, wherein said pair of needles comprises respective projecting portions or nicks close to said needle tips, and wherein said block elements comprise a pair of flexible elements configured to engage and to block said projecting portions or nicks.

9. The surgical tool according to claim 1, wherein said first rod and said second rod are at least partially internal to said elongated body and are coaxial to each other.

10. The surgical tool according to claim 9, wherein said proximal handle comprises a fixed element and a pair of triggers which are operable by traction with respect to said fixed element, said triggers being associated with said first rod and with said second rod, respectively.

11. The surgical tool according to claim 9, wherein said first rod is longer and internal and wherein said second rod is shorter and external.

12. The surgical tool according to claim 1, wherein said suture thread is laterally slippable from said distal end of said elongated body.

13. The surgical tool according to claim 12, wherein said distal end comprises a slot joining said pair of notches and configured to laterally slip and free said suture thread, said suture thread being housed in a tank in said distal end.

14. The surgical tool according to claim 1, wherein said pair of notches are on opposite sides of said elongated body and are longitudinally aligned to each other.

15. The surgical tool according to claim 14, wherein said elongated body has a rounded tip.

16. The surgical tool according to claim 1, wherein said distal end has an ogival profile and is configured for insertion in a hole passing through an abdominal wall, and wherein said pair of notches are tapered with respect to said elongated body to facilitate the insertion and extraction in the hole passing through the abdominal wall, and wherein said pair of notches are further configured to receive fascia margins of said abdominal wall so as to pass through said fascia margins with said pair of needles.

\* \* \* \* \*